(12) United States Patent
Vanek et al.

(10) Patent No.: US 8,911,771 B2
(45) Date of Patent: Dec. 16, 2014

(54) FLUID APPLICATION DEVICE AND METHOD

(75) Inventors: Patrick P. Vanek, Frederick, MD (US);
Henry L. Lewkowicz, Owings Mills, MD (US)

(73) Assignee: Otsuka America Pharmaceutical, Inc., Rockville, MD (US)

(*) Notice: Subject to any disclaimer, the term of this patent is extended or adjusted under 35 U.S.C. 154(b) by 1431 days.

(21) Appl. No.: 11/274,331

(22) Filed: Nov. 16, 2005

(65) Prior Publication Data
US 2006/0115520 A1  Jun. 1, 2006

Related U.S. Application Data

(60) Provisional application No. 60/629,173, filed on Nov. 17, 2004.

(51) Int. Cl.
| | | |
|---|---|---|
| A61F 13/00 | (2006.01) | |
| A61K 45/06 | (2006.01) | |
| A61K 31/79 | (2006.01) | |
| A61F 13/40 | (2006.01) | |
| A61K 31/05 | (2006.01) | |
| A61K 31/155 | (2006.01) | |
| A61K 33/18 | (2006.01) | |
| A61K 31/14 | (2006.01) | |
| A61K 31/17 | (2006.01) | |
| A61K 31/167 | (2006.01) | |
| A61K 31/055 | (2006.01) | |
| A61K 31/045 | (2006.01) | |

(52) U.S. Cl.
CPC .............. *A61M 35/006* (2013.01); *A61K 45/06* (2013.01); *A61K 31/79* (2013.01); *A61K 31/05* (2013.01); *A61K 31/155* (2013.01); *A61K 33/18* (2013.01); *A61K 31/14* (2013.01); *A61K 31/17* (2013.01); *A61K 31/167* (2013.01); *A61K 31/055* (2013.01); *A61K 31/045* (2013.01)
USPC .......................................... 424/443; 424/672

(58) Field of Classification Search
None
See application file for complete search history.

(56) References Cited

U.S. PATENT DOCUMENTS

| | | |
|---|---|---|
| 1,715,914 A | 6/1929 | Halk |
| 2,180,248 A | 11/1939 | Layne |
| 2,218,862 A | 10/1940 | Vredenburgh |
| 2,568,328 A | 9/1951 | Elby |
| 2,783,489 A | 3/1957 | Bogoslowsky |
| 3,386,793 A | 6/1968 | Stanton |
| 3,613,685 A | 10/1971 | Reynolds |
| 3,647,305 A | 3/1972 | Baker et al. |
| 3,647,605 A | 3/1972 | Spiegel |
| 3,687,140 A | 8/1972 | Reynolds |
| 3,757,782 A | 9/1973 | Aiken |

(Continued)

FOREIGN PATENT DOCUMENTS

| | | |
|---|---|---|
| CA | 1284784 | 6/1991 |
| CN | 2280607 Y | 5/1998 |

(Continued)

*Primary Examiner* — Brian Gulledge
(74) *Attorney, Agent, or Firm* — Finnegan, Henderson, Farabow, Garrett & Dunner LLP

(57) ABSTRACT

The present invention provides a device and a method for application of topical antiseptics. The device comprises a handle; a base coupled to the handle; and a substantially hydrophilic foam coupled to the base. The substantially hydrophilic foam is configured to receive the topical antiseptic.

35 Claims, 12 Drawing Sheets

(56) References Cited

U.S. PATENT DOCUMENTS

| | | | |
|---|---|---|---|
| 3,774,609 A | 11/1973 | Schwartzman | |
| 3,826,259 A | 7/1974 | Bailey | |
| 3,891,331 A | 6/1975 | Avery | |
| 3,901,233 A | 8/1975 | Grossan | |
| 3,929,135 A | 12/1975 | Thompson | |
| D245,221 S | 8/1977 | Hoyt | |
| 4,127,339 A | 11/1978 | Malacheski et al. | |
| 4,148,318 A | 4/1979 | Meyer | |
| 4,183,684 A | 1/1980 | Avery, Jr. | |
| 4,219,283 A | 8/1980 | Buckley et al. | |
| 4,291,697 A * | 9/1981 | Georgevich | 604/3 |
| 4,427,115 A | 1/1984 | Laipply | |
| 4,430,013 A | 2/1984 | Kaufman | |
| 4,519,795 A | 5/1985 | Hitchcock, Jr. et al. | |
| 4,594,835 A | 6/1986 | Gray | |
| 4,643,725 A | 2/1987 | Schlesser et al. | |
| D288,780 S | 3/1987 | Miller | |
| 4,648,506 A | 3/1987 | Campbell | |
| 4,696,393 A | 9/1987 | Laipply | |
| 4,701,168 A | 10/1987 | Gammons | |
| D292,672 S | 11/1987 | Duell | |
| 4,812,067 A | 3/1989 | Brown et al. | |
| 4,866,806 A * | 9/1989 | Bedford | 15/104.94 |
| 4,869,612 A | 9/1989 | Mooney et al. | |
| 4,875,602 A | 10/1989 | Chickering et al. | |
| 4,896,768 A | 1/1990 | Anderson | |
| 4,921,137 A | 5/1990 | Heijenga | |
| 4,925,327 A | 5/1990 | Wirt | |
| 4,927,283 A | 5/1990 | Fitjer | |
| 4,957,385 A | 9/1990 | Weinstein | |
| 4,963,045 A | 10/1990 | Willcox | |
| 5,087,138 A | 2/1992 | Terbrusch et al. | |
| 5,098,297 A | 3/1992 | Chari et al. | |
| 5,135,112 A | 8/1992 | Kamen et al. | |
| 5,135,472 A | 8/1992 | Hermann et al. | |
| 5,181,621 A * | 1/1993 | Plaehn | 211/88.01 |
| 5,288,159 A | 2/1994 | Wirt | |
| 5,308,611 A | 5/1994 | Thompson | |
| D351,338 S | 10/1994 | Koptis | |
| 5,376,686 A * | 12/1994 | Ishikawa et al. | 514/635 |
| 5,435,660 A | 7/1995 | Wirt | |
| 5,489,280 A | 2/1996 | Russell | |
| 5,509,744 A | 4/1996 | Frazier | |
| 5,577,851 A | 11/1996 | Koptis | |
| 5,597,255 A | 1/1997 | Yager et al. | |
| 5,616,348 A | 4/1997 | Winicov | |
| 5,658,084 A | 8/1997 | Wirt | |
| D386,849 S | 11/1997 | Dehavilland | |
| 5,702,404 A * | 12/1997 | Willingham | 606/122 |
| 5,713,843 A | 2/1998 | Vangsness | |
| D396,126 S | 7/1998 | Ohmart | |
| 5,775,826 A | 7/1998 | Miller | |
| D396,911 S | 8/1998 | DeHavilland | |
| 5,791,801 A | 8/1998 | Miller | |
| 5,800,825 A | 9/1998 | McMullen | |
| 5,829,902 A | 11/1998 | Fomby | |
| 5,908,256 A | 6/1999 | Bernstein | |
| 5,916,882 A | 6/1999 | Jeng | |
| D416,389 S | 11/1999 | Frazier | |
| 6,019,765 A | 2/2000 | Thornhill et al. | |
| 6,039,488 A | 3/2000 | Krawczyk et al. | |
| 6,126,633 A | 10/2000 | Kaji et al. | |
| D434,525 S | 11/2000 | Angeletta | |
| 6,155,990 A | 12/2000 | Fournier | |
| 6,248,085 B1 | 6/2001 | Scholz et al. | |
| D448,521 S | 9/2001 | Angeletta | |
| 6,315,480 B1 | 11/2001 | Martel et al. | |
| 6,371,675 B1 | 4/2002 | Hoang et al. | |
| 6,415,470 B1 | 7/2002 | Ramrattan | |
| 6,419,642 B1 | 7/2002 | Marchitto et al. | |
| 6,422,778 B2 | 7/2002 | Baumann et al. | |
| D461,596 S | 8/2002 | Angeletta | |
| D467,613 S | 12/2002 | Indegno et al. | |
| 6,488,665 B1 | 12/2002 | Severin et al. | |
| 6,503,013 B2 | 1/2003 | Strauss | |
| 6,505,985 B1 | 1/2003 | Hidle et al. | |
| 6,523,550 B2 | 2/2003 | McCormick | |
| 6,533,484 B1 | 3/2003 | Osei et al. | |
| 6,536,975 B1 | 3/2003 | Tufts | |
| 6,546,588 B1 * | 4/2003 | Black | 15/244.1 |
| 6,547,468 B2 | 4/2003 | Gruenbacher et al. | |
| 6,595,940 B1 | 7/2003 | D'Alessio et al. | |
| D481,165 S | 10/2003 | Angeletta | |
| D481,166 S | 10/2003 | Angeletta | |
| 6,672,784 B2 | 1/2004 | Baumann et al. | |
| 6,682,695 B2 | 1/2004 | MacPhee et al. | |
| 6,708,822 B1 | 3/2004 | Muni | |
| D490,561 S | 5/2004 | Angeletta | |
| D490,562 S | 5/2004 | Angeletta | |
| 6,729,786 B1 | 5/2004 | Tufts et al. | |
| 6,773,189 B1 | 8/2004 | Tsaur | |
| D498,021 S | 11/2004 | Angeletta | |
| 6,902,335 B2 | 6/2005 | Bergey et al. | |
| 6,910,822 B2 | 6/2005 | Hidle et al. | |
| 6,916,133 B2 | 7/2005 | Hoang et al. | |
| 6,929,475 B1 | 8/2005 | Dragan | |
| 6,960,041 B2 | 11/2005 | Tsaur | |
| D512,794 S | 12/2005 | Angeletta | |
| 6,991,393 B2 | 1/2006 | Tufts et al. | |
| 6,991,394 B2 | 1/2006 | Tufts et al. | |
| 6,992,233 B2 | 1/2006 | Drake et al. | |
| D519,283 S | 4/2006 | Watson | |
| 7,040,827 B2 | 5/2006 | Gueret | |
| D527,489 S | 8/2006 | Angeletta | |
| 7,090,422 B2 | 8/2006 | Baumann et al. | |
| D527,842 S | 9/2006 | Angeletta | |
| 7,108,440 B1 | 9/2006 | Gruenbacher et al. | |
| D536,481 S | 2/2007 | Angeletta | |
| 7,182,536 B2 | 2/2007 | Tufts et al. | |
| 7,201,525 B2 | 4/2007 | Mohiuddin | |
| D543,658 S | 5/2007 | Angeletta | |
| D547,003 S | 7/2007 | Angeletta | |
| 7,261,701 B2 * | 8/2007 | Davis et al. | 604/3 |
| D558,393 S | 12/2007 | Angeletta | |
| D566,330 S | 4/2008 | Angeletta | |
| 7,377,710 B2 | 5/2008 | Baumann et al. | |
| 2001/0012851 A1 | 8/2001 | Lundy et al. | |
| 2001/0050083 A1 | 12/2001 | Marchitto et al. | |
| 2001/0055511 A1 * | 12/2001 | Baumann et al. | 401/266 |
| 2002/0044816 A1 | 4/2002 | Strauss | |
| 2002/0076255 A1 | 6/2002 | Hoang et al. | |
| 2002/0114657 A1 | 8/2002 | Gueret | |
| 2003/0086747 A1 | 5/2003 | Baumann et al. | |
| 2003/0095826 A1 * | 5/2003 | Policicchio et al. | 401/138 |
| 2003/0123919 A1 | 7/2003 | Gueret | |
| 2004/0068218 A1 | 4/2004 | Davis et al. | |
| 2004/0071494 A1 | 4/2004 | Staniforth et al. | |
| 2004/0074033 A1 * | 4/2004 | Steinberg | 15/144.4 |
| 2004/0086321 A1 | 5/2004 | Burkholz et al. | |
| 2004/0114988 A1 | 6/2004 | Baumann et al. | |
| 2004/0162533 A1 * | 8/2004 | Alley | 604/290 |
| 2004/0186183 A1 | 9/2004 | Johnson | |
| 2004/0223801 A1 | 11/2004 | Detwiler et al. | |
| 2004/0230168 A1 | 11/2004 | Keaty, Jr. et al. | |
| 2004/0240927 A1 | 12/2004 | Hoang et al. | |
| 2004/0253039 A1 | 12/2004 | Stenton | |
| 2004/0265388 A1 * | 12/2004 | Zhang et al. | 424/486 |
| 2005/0003178 A1 | 1/2005 | Detert et al. | |
| 2005/0047845 A1 | 3/2005 | White et al. | |
| 2005/0049538 A1 | 3/2005 | Trevillot | |
| 2006/0072962 A1 | 4/2006 | Cybulski et al. | |
| 2006/0115520 A1 | 6/2006 | Vanek et al. | |
| 2006/0147250 A1 | 7/2006 | Tereschouk | |
| 2006/0247568 A1 | 11/2006 | Stenton | |
| 2007/0020029 A1 | 1/2007 | Baumann et al. | |
| 2007/0147946 A1 | 6/2007 | Cybulski et al. | |
| 2007/0147947 A1 | 6/2007 | Stenton et al. | |
| 2008/0119801 A1 | 5/2008 | Moore | |
| 2009/0008021 A1 | 1/2009 | Detert et al. | |

FOREIGN PATENT DOCUMENTS

| | | |
|---|---|---|
| DE | 19860759 | 6/2000 |
| EP | 0 232 596 A1 | 8/1987 |

(56) References Cited

FOREIGN PATENT DOCUMENTS

| EP | 0 507 317 A2 | 10/1992 |
| EP | 1 721 582 A1 | 11/2006 |
| GB | 2 272 644 A | 5/1994 |
| JP | 1080375 | 3/1989 |
| JP | 7307311 | 11/1995 |
| JP | 9028716 | 2/1997 |
| WO | WO 99/63934 | 12/1999 |
| WO | WO 01/74437 | * 10/2001 ............ A61M 35/00 |
| WO | WO 01/74437 A1 | 10/2001 |
| WO | WO 03/092784 A1 | 11/2003 |
| WO | WO 2004/094494 | 11/2004 |
| WO | WO 2004/110545 A1 | 12/2004 |
| WO | WO 2005/099808 A1 | 10/2005 |

* cited by examiner

FLUID APPLICATION DEVICE AND METHOD

RELATED APPLICATIONS

The present application claims priority to U.S. Provisional Application 60/629,173, "Fluid Application Device and Method," filed on Nov. 17, 2004, by Patrick P. Vanek and Henry L. Lewkowicz, herein incorporated by reference in its entirety.

FIELD

The present application relates to an apparatus and method for fluid application.

INTRODUCTION

Preparation of patients for various medical procedures, e.g., surgery, typically includes application of a topical solution (or fluid), e.g., an antiseptic solution, to sanitize the area targeted for medical procedures. Topical solutions may be applied to the targeted area by saturating a sponge-like material with the solution and using a handheld device, for example a pair of forceps or a hemostat, to direct the saturated sponge to the targeted area. The sponges or foam materials are typically soaked in a fluid contained within an open pan or other container.

In certain instances, existing devices used to apply solutions exhibit various disadvantages. For example, typical applicators utilize sponges that do not retain fluid efficiently, resulting in leakage. As a result, preparation of targeted areas for antiseptic cleaning becomes a messy procedure. In addition, leakage of various fluids onto areas outside of the targeted areas can lead to pooling of the various fluids which may cause irritation or discomfort.

Another example of a disadvantage involves the difficulty of dispensing a desired dose of fluid at the targeted area. During fluid application, in certain instances, it may be desirable to control the amount of fluid, e.g., antiseptic solution, that is dispensed from the applicator. However, because existing applicators dispense fluid inefficiently, the precise amount of solution delivered to the targeted area may be difficult to determine. This may result in either more or less solution applied to the targeted area than is desired. In addition, typical applicators utilize foams and/or fluid delivery systems that fail to timely dispense a precise amount of fluid. For example, certain applicators with internal ampoules that store fluid take time for the fluid to saturate the sponge and thus be available for application to the patient. This can result in unpredictable and imprecise dispensing of the desired solution.

SUMMARY

According to certain embodiments, an applicator device for applying a fluid comprises a handle comprising a proximate end and a distal end, a base coupled to the proximate end of the handle, and a substantially hydrophilic foam coupled to the base, wherein the substantially hydrophilic foam is configured to receive the fluid.

According to certain embodiments, an applicator device can be supplied ready to use, i.e., without the need for additional manipulation beyond removing the device from its packaging, if any.

According to certain embodiments, an applicator system comprises an applicator device for applying a fluid comprising a handle that comprises a proximate end and a distal end, a base coupled to the proximate end of the handle, a substantially hydrophilic foam coupled to the base, wherein the substantially hydrophilic foam is configured to receive the fluid, and a storage device configured to receive the applicator device.

According to certain embodiments, a method of applying a fluid comprises introducing a fluid to a substantially hydrophilic foam and depositing a desired portion of the fluid onto a targeted area.

DESCRIPTION OF VARIOUS EMBODIMENTS

Figure 1A:
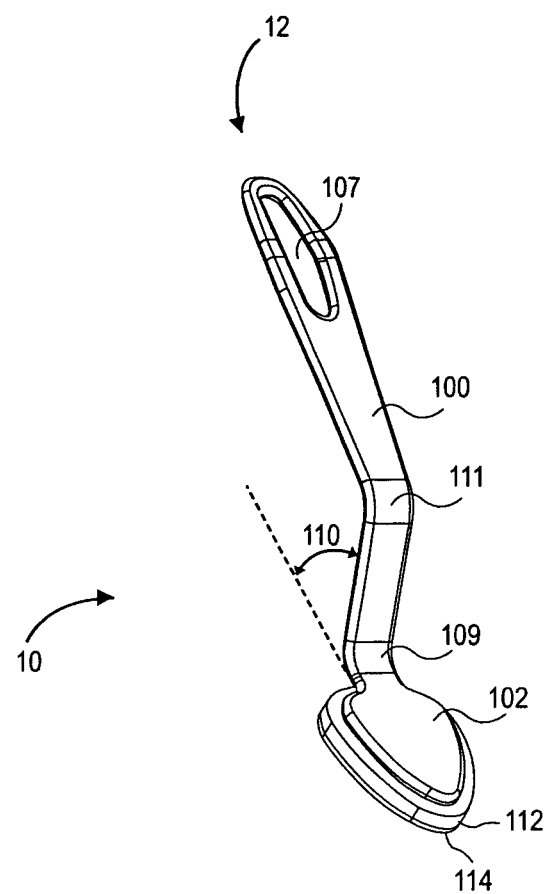
FIG. 1A illustrates a perspective view of an applicator device according to certain embodiments.

In this application, the use of the singular includes the plural unless specifically stated otherwise. In this application, the use of "or" means "and/or" unless otherwise stated. Furthermore, the use of the term "including," as well as other forms, such as "includes" or "included," is not limiting. Also, terms such as "element" or "component" encompass both elements and components comprising one unit and elements and components that comprise more than one subunit unless specifically stated otherwise. Wherever possible, the same reference numbers will be used throughout the drawings to refer to the same or like parts.

The section headings used herein are for organizational purposes only, and are not to be construed as limiting the subject matter described. All documents cited in this application, including, but not limited to patents, patent applications, articles, books, and treatises, are expressly incorporated by reference in their entirety for any purpose.

The term "fluid" as used herein refers to a liquid that in certain embodiments may be used to sanitize a region in preparation for various medical procedures. The liquid may be an antiseptic solution containing an active ingredient. Various antiseptic solution active ingredients are known in the art, including, but not limited to, ethanol, isopropyl alcohol, other alcohols, and combinations thereof; benzalkonium chloride; benzethonium chloride; chlorhexidine gluconate; chlorhexidine gluconate with alcohol; chloroxylenol; cloflucarban; fluorosalan; hexachlorophene; hexylresorcinols; iodine-containing compounds; povidone iodine; povidone iodine with alcohol, ethanol, isopropyl alcohol and other alcohols, and combinations thereof.

In certain embodiments, the antiseptic solution may include a biguanide derivative and/or salts thereof, e.g., olanexidine [1-(3,4-dichlorobenzyl)-5-octylbiguanide] and salts thereof, as the active ingredient, as disclosed, for example in U.S. Pat. No. 5,376,686. The antiseptic solution may also incorporate certain surfactants, for example, polyoxyethylene-based nonionic surfactants, and/or alcohols, for example, ethanol, isopropyl alcohol and other alcohols, and/or water, in varying amounts. Useful surfactants are known to one skilled in the art, for example, Poloxamer 124 (a/k/a Polyoxypropylene-polyoxyethylene Block Copolymer 124), which is available as Polyoxyethylene(20) polyoxypropylene(20) glycol from Asahi Denka Co., Ltd., Japan, POE (9) lauryl ether (available as 'BL-9EX' from Nikko Chemicals Co., Ltd., Tokyo, Japan), POE (10) lauryl ether, also known as nonoxynol-10, or NP-10, (available as 'Emulin NL-100' from Sanyo Chemical Industries, Ltd., Kyoto Japan).

In certain embodiments, the antiseptic solution may include an active ingredient and a polyoxyethylene-based nonionic surfactant in various concentrations. For example, in certain embodiments, the biguanide derivative and/or salts thereof may be present at a concentration of about 0.05 to about 5.0% (w/v of biguanide base) and the polyoxyethylene-based nonionic surfactant may be present at a concentration of about 0.05 to about 16% (w/v).

The term "substantially hydrophilic foam" as used herein refers to a polymer-based foam that has an affinity for water. For example, certain embodiments of the invention can utilize a polyurethane foam with an open-cell pore structure. In certain instances, the substantially hydrophilic foam can be designed for a high rate of fluid absorption such as, for example, absorption of around 20 times the weight of the foam. While not wishing to be bound by theory, a substantially hydrophilic foam can demonstrate an affinity for water through one or more mechanisms including, but not limited to, the presence of polar groups in the polymer chains that can form hydrogen bonds with water or liquids containing active protons and/or hydroxyl groups, a fine open-cell pore structure that channels liquid into the body of the foam structure by capillary forces, and/or the addition of absorbing materials, such as super absorbers and/or surfactants, to the foam matrix. Substantially hydrophilic foams that can be utilized in certain embodiments of the invention are available from organizations including the following: Rynel, Inc. (Boothbay, Me.), Avitar, Inc. (Canton, Mass., USA), Lendell Manufacturing, Inc. (Charles, Mich., USA), and Copura (Denmark). In addition, certain patents, including U.S. Pat. No. 5,135,472 to Hermann, et al., disclose substantially hydrophilic foams that may be utilized in certain embodiments of the invention.

Figure 4A:
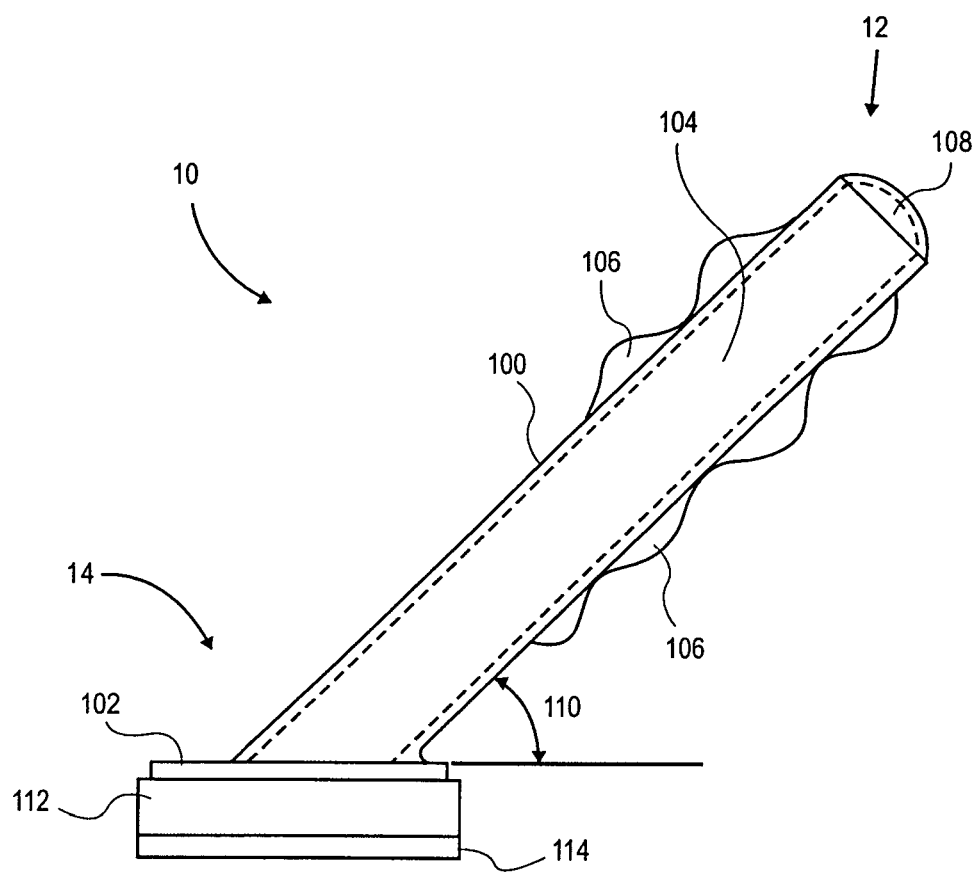
FIG. 4A illustrates a side view of an applicator device according to certain embodiments.

According to certain embodiments, as illustrated in FIG. 1A or 4A, an applicator device 10 may comprise a handle 100, a base 102, and a substantially hydrophilic foam 112. Handle 100 may comprise various cross-sectional geometries, including, but not limited to, circular, oval, rectangular, triangular, polygonal, and/or complex shapes that include combinations thereof. In certain embodiments, handle 100 may be generally smooth along its length. As illustrated by FIG. 4A, in certain embodiments, handle 100 may include various indentations and/or protrusions 106 along its length to facilitate, for example, a user's manipulation of applicator device 10. Indentations and/or protrusions 106 may exist at various locations around the circumference of handle 100. In certain embodiments, at least a portion of handle 100 may include a surface coating, for example rubber, to facilitate the use of applicator device 10. In certain embodiments, at least a portion of handle 100 may include a texture applied to the surface of handle 100 to, e.g., help transport any unwanted liquid away from handle 100 and allow the user to obtain a secure grip.

Figure 1B:
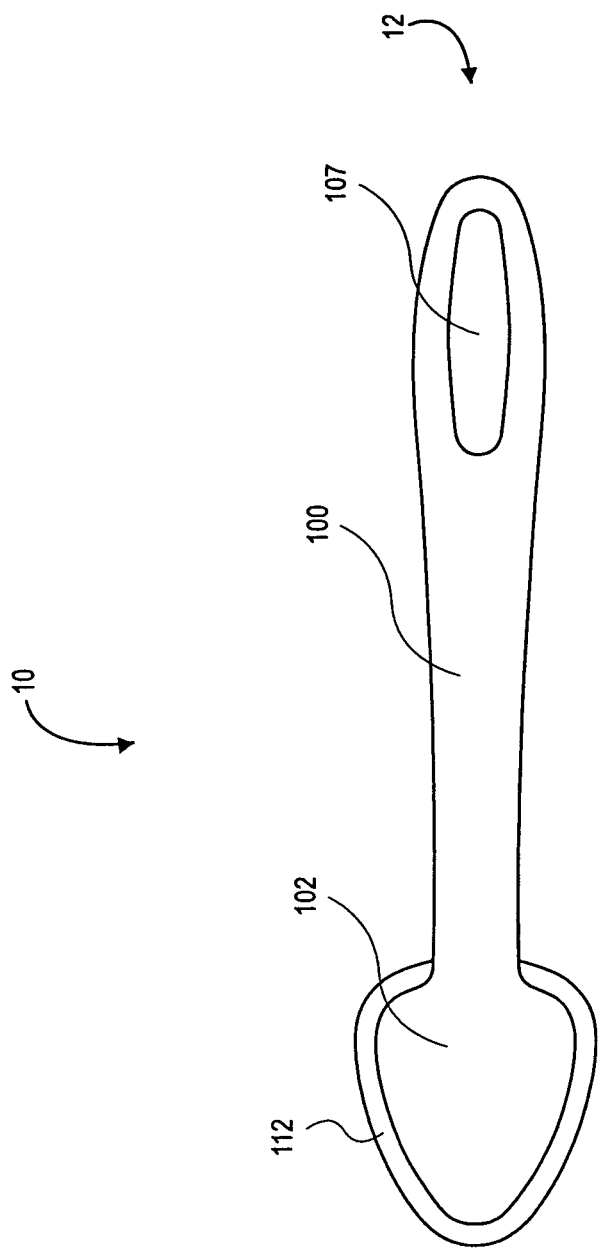
FIG. 1B illustrates a top view of an applicator device according to certain embodiments.
Figure 1C:
FIG. 1C illustrates a side view of a substantially hydrophilic foam, according to certain embodiments.
Figure 1D:
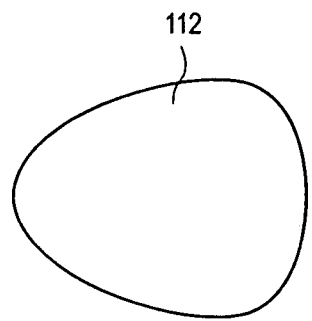
FIG. 1D illustrates a top view of a substantially hydrophilic foam, according to certain embodiments.

In certain embodiments, as illustrated in FIGS. 1A-1B, handle 100 may define an opening 107. In certain embodiments, opening 107 may comprise various shapes including, but not limited to, elliptical, circular, rectangular, polygonal, and the like. In certain embodiments, opening 107 may allow for a number of different gripping positions.

Figure 5B:
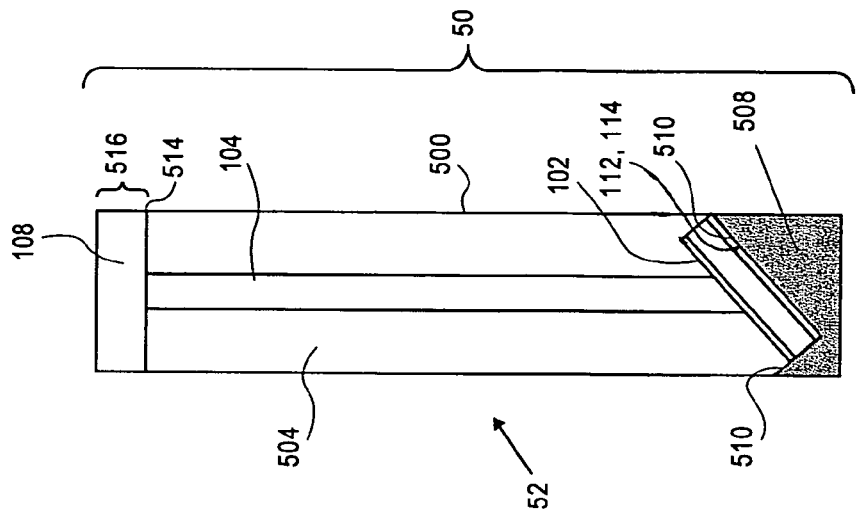
FIG. 5B illustrates a side view of an applicator system with an applicator device, according to certain embodiments.
Figure 5A:
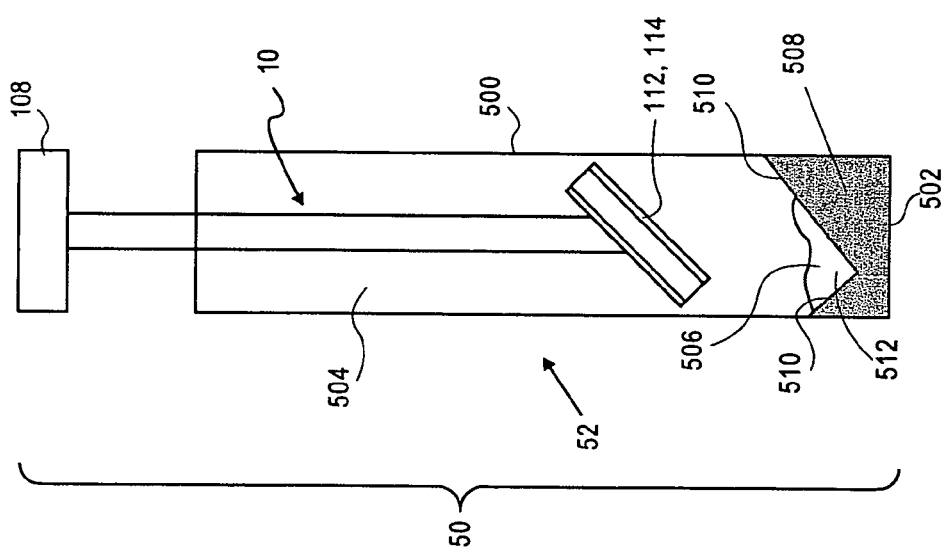
FIG. 5A illustrates a side view of an applicator system with an applicator device partially removed, according to certain embodiments.

According to certain embodiments, illustrated in FIG. 4A, handle 100 may include a distal end 12 that can define an endpiece 108. Endpiece 108 may, in certain embodiments, be an integral part of handle 100 such as, for example, an end to a solid rod or tube. In certain embodiments, endpiece 108 may be a separate piece from handle 100 that attaches to handle 100. As illustrated in FIG. 5A, in certain embodiments endpiece 108 may comprise a larger cross-sectional size than handle 100 to, for example, allow for endpiece 108 to sealably interface with a storage device 52. In certain embodiments, endpiece 108 may have a smaller cross-sectional size than handle 100 to, for example, allow for endpiece 108 to slide at least partially within handle 100. Non-limiting exemplary embodiments of certain attachments of endpiece 108 to handle 100 include press-fits, interference-fits, mechanical interlocks, hinges, keyways, threaded passages, and the like, or combinations thereof.

Figure 6C:
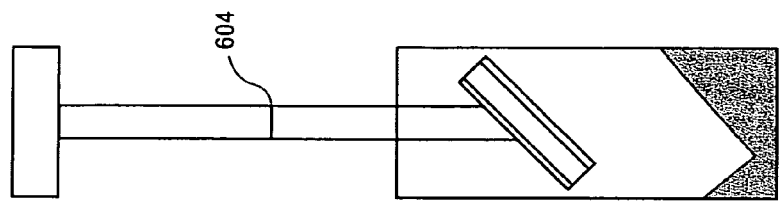
FIG. 6C illustrates a side view of an applicator system with an extended handle with an applicator device partially removed, according to certain embodiments.
Figure 6B:
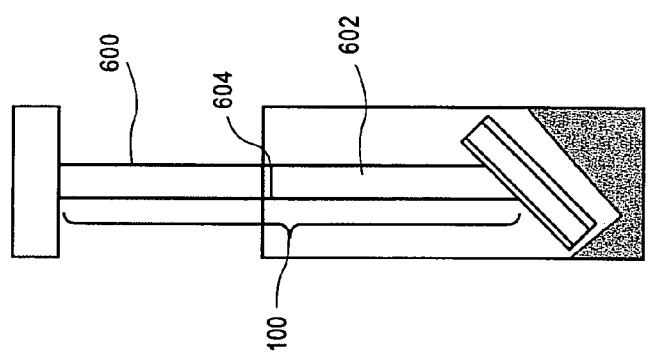
FIG. 6B illustrates a side view of an applicator system with a retractable handle in an extended position, according to certain embodiments.
Figure 6A:
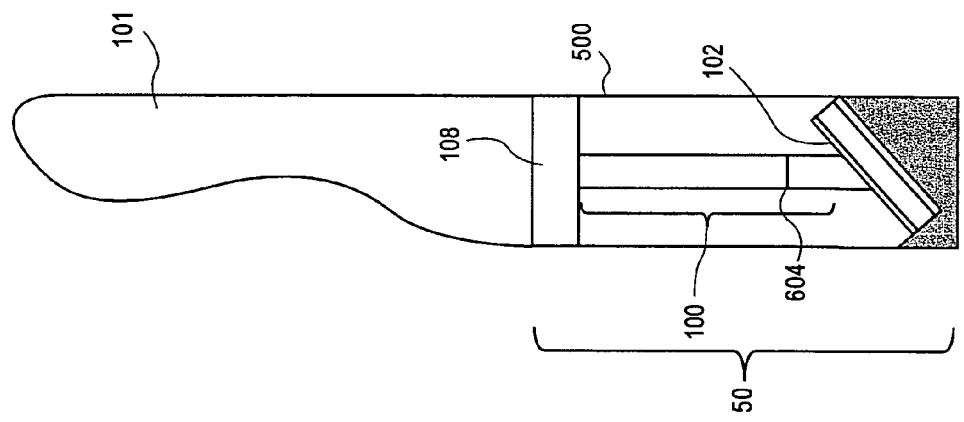
FIG. 6A illustrates a side view of an applicator system with a retracted handle, according to certain embodiments.

In certain embodiments, as illustrated in FIG. 6A, a second handle 101 can couple to endpiece 108. In certain embodiments, second handle 101 and endpiece 108 can form one contiguous piece. In certain embodiments, second handle 101 can incorporate certain ergonomic considerations. For example, second handle 101 can be shaped in a manner to facilitate a user's grip of applicator device 10. Although FIG. 6A illustrates one possible shape to accomplish such considerations, one skilled in the art can vary this shape in a number of ways to accomplish the same result.

In certain embodiments, as illustrated in FIG. 1A, handle 100 may include one or more deviations, such as, for example, curves, bends, angles, and the like, at various positions along the length of handle 100. In certain embodiments, these deviations may exist along multiple axes or along a single axis, and may facilitate, e.g., ergonomic considerations. For example, in certain embodiments, handle 100 may include a first bend 109 generally along the vertical axis. In certain embodiments, as discussed in more detail below, first bend 109 may define an angle 110 with the horizontal axis. In certain embodiments, handle 100 may define a second bend 111. In certain embodiments, second bend 111 may align handle 100 with the horizontal axis. In certain embodiments, an extended handle (not shown) may be attached to handle 100 to allow for various considerations, including, but not limited to, greater leverage and/or reach. In certain embodiments, as illustrated in FIG. 4A, handle 100 may not comprise any deviations. In other words, handle 100 may be generally straight.

In certain embodiments, handle 100 may comprise a solid piece, such as, for example, a solid rod. In certain embodiments, as illustrated in FIG. 4A, at least a portion of handle 100 may include a hollow region 104. Hollow region 104 may be configured to receive fluid directly or indirectly. In certain embodiments, directly receiving fluid can be directly received by, for example, pouring and/or injecting fluid into hollow region 104. In certain embodiments, fluid can be injected into hollow region 104 through, for example, a substantially sealable membrane located along the length of handle 100 and/or at distal end 12. In certain embodiments, fluid can be indirectly received by, for example, inserting a fluid-containing device such as, for example, a cartridge or other container, at least partially within hollow region 104. In certain embodiments, such cartridge or container may form part of endpiece 108.

According to certain embodiments, handle 100 and/or base 102 may be made of numerous materials including, but not limited to, metals, metal-alloys, plastics and other polymers, including, for example, nylon, composite materials, or any combination thereof. Handle 100 may be made by various manufacturing processes known in the art including, but not limited to, molding, injection molding, machining, casting, extruding, and/or combinations thereof.

According to certain embodiments, handle 100 may couple to base 102. In certain embodiments, base 102 may be an integral part of handle 100. An integral base/handle combination may be manufactured by various processes known in the art, including, but not limited to, molding, injection molding, casting, machining, or combinations thereof. In certain embodiments, handle 100 may couple to base 102 in a variety of ways known in the mechanical arts, including, but not limited to, attachments by hinges, adhesives, mechanical interlocks, threaded portions, press-fits, friction-fits, interference fits, slide-fits, and/or combinations thereof.

In certain embodiments, applicator device 10 may include an interchangeable attachment between handle 100 and base 102. An interchangeable attachment may, for example, facilitate the use of variously sized bases 102 on the same handle 100, and vice versa. This may facilitate, e.g., the use of differently-sized substantially hydrophilic foams 112 with the same handle 100.

Figure 4B:
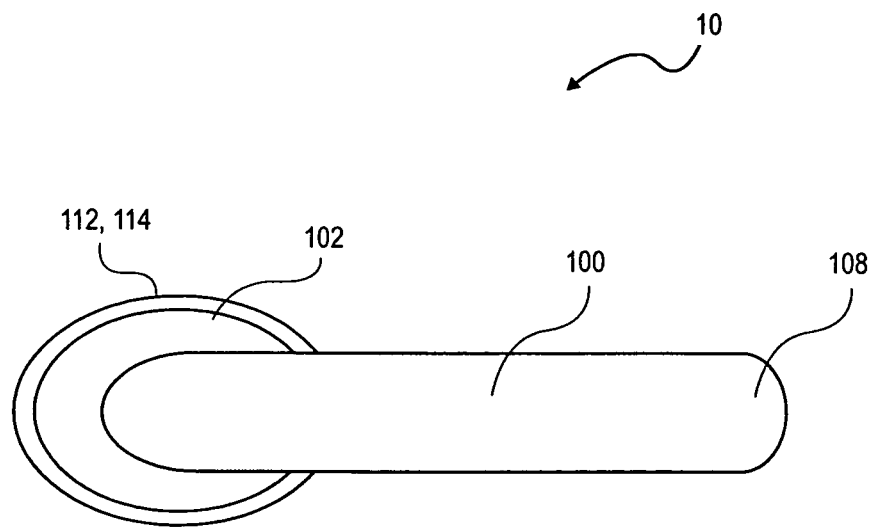
FIG. 4B illustrates a top view of an applicator device according to certain embodiments.
Figure 4C:
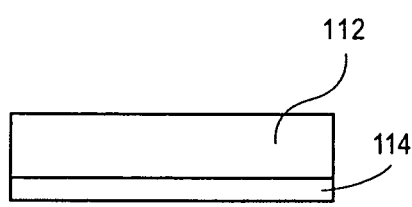
FIG. 4C illustrates a side view of a substantially hydrophilic foam, according to certain embodiments.
Figure 4D:
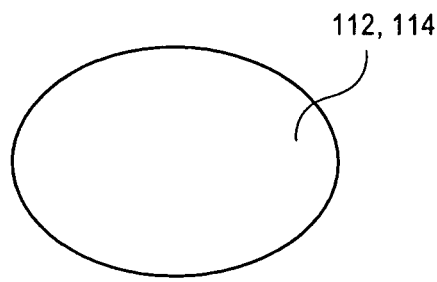
FIG. 4D illustrates a top view of a substantially hydrophilic foam, according to certain embodiments.

In certain embodiments, base 102 may comprise a variety of shapes. For example, as illustrated in certain embodiments in FIGS. 1B and 4B, the shape of base 102 may be generally triangular with rounded edges. Other examples of shapes for base 102 include, but are not limited to, rectangular, circular, oval, various polygonal shapes, and/or complex shapes comprising a combination thereof.

According to certain embodiments, handle 100 and base 102 may define an angle 110. Although FIGS. 1A and 4A illustrate angle 110 at approximately 45 degrees, certain embodiments comprise angles within the range of 0 to 180 degrees. Allowing angle 110 to vary over a wide range gives flexibility to the design of applicator 100 to accommodate various factors such as, for example, ergonomic factors. In certain embodiments, the attachment of handle 100 to base 102 through hinge-like connections may facilitate a plurality of angles 110. In certain embodiments, the hinge-like connections may comprise lockable positions, allowing for applicator device 10 to be used at an intermediate angle.

In certain embodiments, base 102 may couple to substantially hydrophilic foam 112 by many mechanisms, such as, for example, adhesive bonding, fusion bonding, mechanical interlocks, hook-and-loop mechanisms (e.g., Velcro®), threaded pieces, and the like.

In certain embodiments, a user may dispense fluid contained in substantially hydrophilic foam 112 by pressing on, and thereby compressing, the substantially hydrophilic foam. As a result, compression of substantially hydrophilic foam 112, in certain embodiments, may facilitate the dispensing of fluid retained by substantially hydrophilic foam 112. In certain embodiments, the volume of substantially hydrophilic foam 112 can determine the amount of fluid (i.e., to dispense a desired amount of fluid) that can be dispensed from substantially hydrophilic foam 112. That is, if one desires an applicator that dispenses a larger amount of fluid, the volume of substantially hydrophilic foam 112 can be increased (i.e., increase the desired amount). Also, if one desires an applicator that dispenses a smaller amount of fluid, the volume of substantially hydrophilic foam 112 can be decreased (i.e., decrease the desired amount). For example, as illustrated in certain embodiments in FIGS. 1C-1D and 4C-4D, the thickness of substantially hydrophilic foam 112 may vary, while the cross sectional area of substantially hydrophilic foam 112 remains constant, to facilitate dispensing a varied amount of fluid that generally corresponds to the thickness variation of substantially hydrophilic foam 112. Alternatively, both the thickness and the cross sectional area of substantially hydrophilic foam 112 may be varied in order to vary the amount of liquid dispensed.

According to certain embodiments, an abrasion layer 114 may be coupled to substantially hydrophilic foam 112. In certain embodiments, abrasion layer 114 may abrade an area targeted for treatment, for example the epidermis. Abrasion may occur before, during, and/or after dispensing the fluid. In certain embodiments, abrasion may cause a loosening of certain biologic materials, for example body oils, body soils, and/or bacteria, to facilitate treatment of the targeted area. For example, before application of an antiseptic solution, a user may abrade the epidermis of a patient to loosen bacteria in order to improve the efficacy of the antiseptic process. In certain embodiments, abrasion layer 114 may comprise more than one layer of material, which may facilitate a greater amount of abrasion and/or abrasion of harder to clean areas. In certain embodiments, abrasion layer 114 may comprise various textures and/or weaves, for example, a gauze-like material. In certain embodiments, abrasion layer 114 may be made from various materials that facilitate abrasion, including, but not limited to, cotton, rayon, nylon, and/or combinations thereof. In certain embodiments, the material that abrasion layer 114 is made from can be chosen from a number of materials that exhibit varying degrees of abrasiveness. For example, the skin of a premature baby can be thin and fragile, thus an applicator device that comprises an abrasion layer made from nylon or rayon may be preferable to an abrasion layer made from cotton. In certain embodiments, abrasion layer 114 may comprise a plurality of layers of different materials.

As illustrated in certain embodiments in FIGS. 1A-1C and 4A-4C, abrasion layer 114 may have a shape that generally corresponds to the shape of substantially hydrophilic foam 112. However, in certain embodiments, abrasion layer 114 may have various other shapes including, but not limited to, circular, oval, rectangular, triangular, polygonal, and the like, or complex shapes including one or more of the same. In certain embodiments, abrasion layer 114 may couple to substantially hydrophilic foam 112 by various attachment mechanisms including, but not limited to, adhesive bonding, fusion bonding, mechanical interlocks, hook-and-loop mechanisms (e.g., Velcro®), threaded pieces, and the like. In certain embodiments, abrasion layer 114 may be laminated to substantially hydrophilic foam 112. Lamination and/or attachment of various materials to foams is known in the art. For example, U.S. patent application Ser. No. 10/829,919, U.S. Provisional Application No. 60/464,306, and PCT Serial No. US04/012474 all disclose methods and apparatuses for attaching materials to polyurethane foam.

Figure 2A:
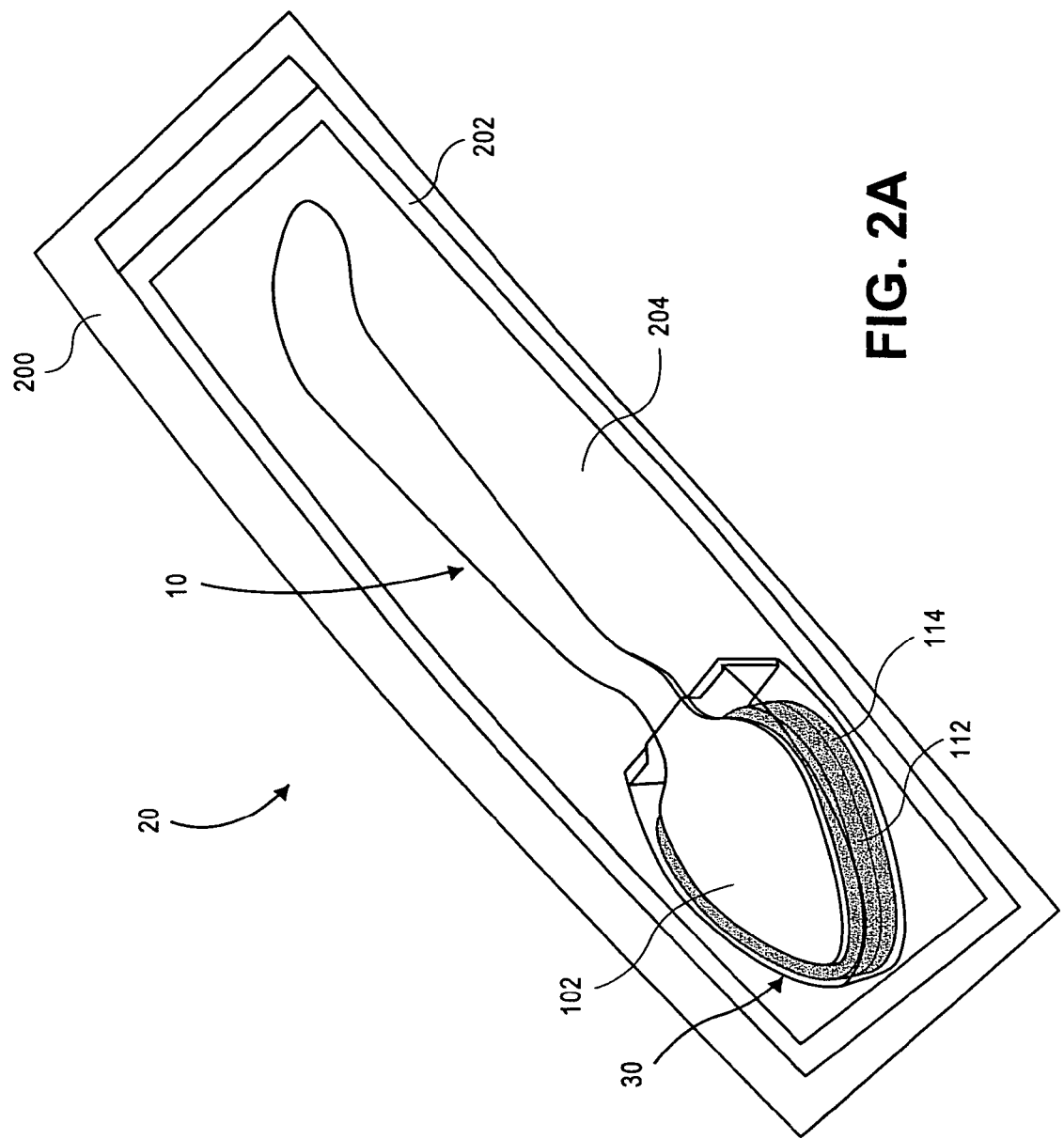
FIG. 2A illustrates a perspective view of an applicator system, according to certain embodiments.
Figure 2B:
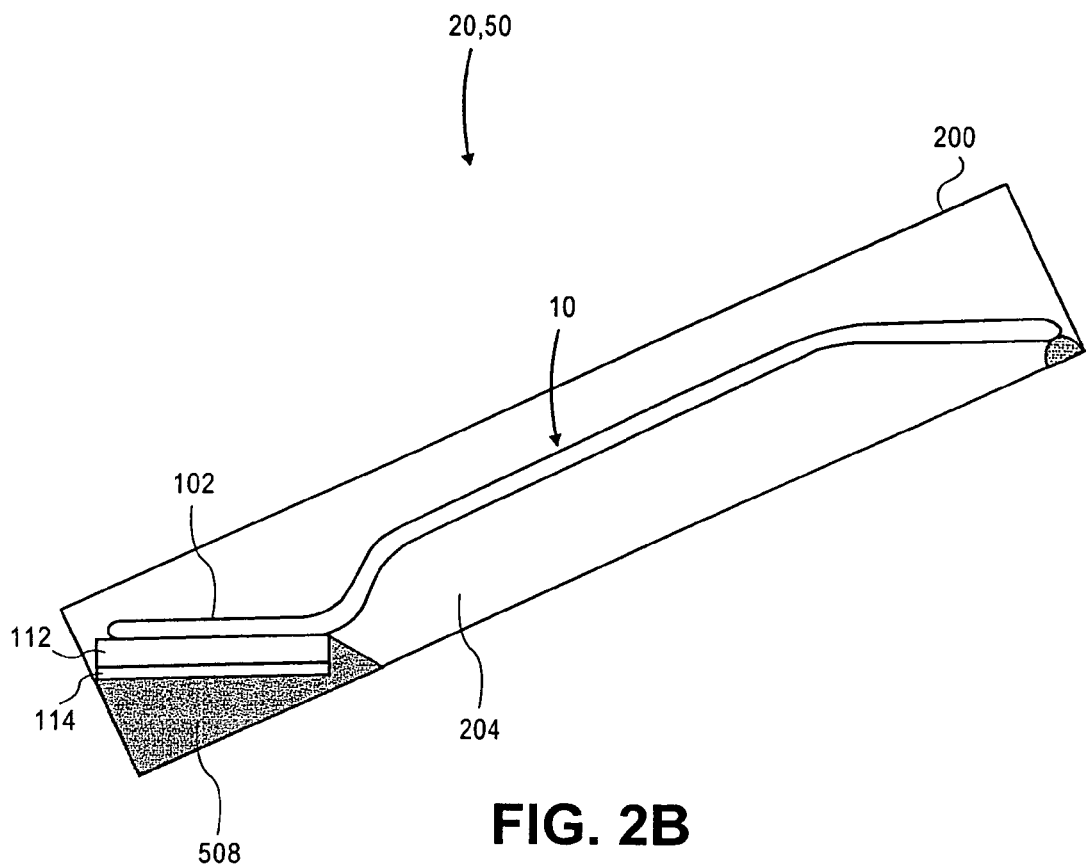
FIG. 2B illustrates a side view of an applicator system, according to certain embodiments.

In certain embodiments, as illustrated in FIGS. 2A and 2B, an applicator system 20 may comprise applicator device 10, a sealable container 200, and a storage device 30. In certain embodiments, sealable container 200 may be configured to receive applicator device 10. In certain embodiments, sealable container 200 may comprise a seal 202 that may define a sealed region 204 wherein applicator device 10 may be kept. In certain embodiments, sealable container 200 may be a removable cover and/or a container, either of which can be flexible and/or rigid. For example, FIG. 2B illustrates a rigid, sealable container 200 with a bottom and side walls that can be made from high-density polyethylene and other polymers, or combinations thereof and a top made from laminated aluminum foil or other appropriate lidding materials, Tyvek, plastics and the like. In certain embodiments, sealable container 200 may be made from any material that can prevent outside contaminants from entering sealed region 204 including, but not limited to, one or more polymer-based materials (e.g., plastic trays), Tyvek, metallic constructs, laminated constructs, paper, and/or any combinations thereof.

In certain embodiments, an applicator system can be provided to the user in ready-to-use form. For example, as illustrated in FIGS. 2A and 2B, an applicator device 10 can reside within a sealable container 200 with a pre-measured amount of fluid retained by a substantially hydrophilic foam 112 and/or an abrasion layer 114. Thus, a user can simply open the sealable container to gain access to the applicator device and begin using the applicator device, without the need for any additional manipulation of the applicator device. Similarly, as illustrated in exemplary embodiments in FIGS. 5A-8B, the applicator device 10 can reside within a storage device 52 that comprises a wall 500. The storage device 52 can contain a pre-measured amount of fluid 506 for retention by substantially hydrophilic foam 112 and/or an abrasion layer 114. As is discussed in more detail below, the wall 500 can form a seal 516 (see, e.g., FIG. 5B) with an endpiece 108 of the applicator device 10. Thus, a user can simply remove the applicator device 10 from the storage device 52, thereby unsealing the endpiece 108 from the wall 500. As a consequence, these configurations can promote the efficient use of the applicator device in a wide variety of operating conditions.

In certain embodiments, as illustrated in FIGS. 2A, 2B, 3A and 3B, storage device 30 may be configured to receive base 102, substantially hydrophilic foam 112, and/or abrasion layer 114. In certain embodiments, storage device 30 may be made from a rigid material that generally prevents substantially hydrophilic foam 112 and/or abrasion layer 114 from being substantially compressed. Rigid materials consistent with certain embodiments of storage device 30 include, but are not limited to, metals, plastics and other polymers, glass, composite materials, and combinations thereof. In certain embodiments, storage device 30 may comprise a body 300 and a closure 302. In certain embodiments, storage device 30 may define an inner portion 304 within which at least a portion of applicator device 10 can reside. In certain embodiments, body 300 may be shaped in a manner so as to facilitate the placement of base 102, substantially hydrophilic foam 112, and/or abrasion layer 114 within inner portion 304. In certain embodiments, closure 302 may open and/or close at a hinge 303 to facilitate enclosure of base 102, substantially hydrophilic foam 112, and/or abrasion layer 114 within inner portion 304. In certain embodiments, closure 302 may define a recess 306 to allow for handle 100 to pass through storage device 30.

Figure 3A:
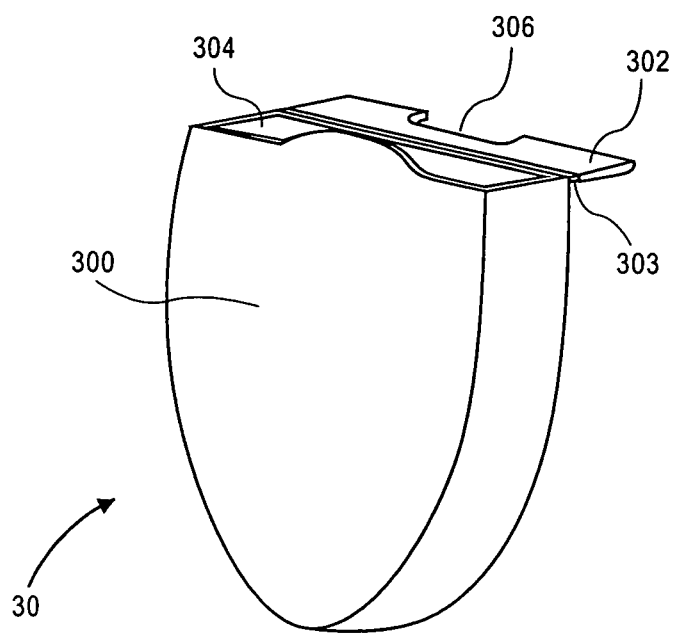
FIG. 3A illustrates a perspective view of a rigid container, according to certain embodiments.
Figure 3B:
FIG. 3B illustrates a side view of a rigid container, according to certain embodiments.

In certain embodiments, recess 306 can incorporate a seal (not shown) to substantially contain fluid within inner portion 304 and/or to substantially prevent entry of certain microbes into inner portion 304. In certain embodiments, the seal can be generally compliant so as to conform around handle 100. In certain embodiments, closure 302 can define a tab 305. In certain embodiments, as illustrated in FIG. 3B, tab 305 can extend beyond a top surface 301 of body 300. In certain embodiments, tab 305 can facilitate a user's opening and/or closing of closure 302. For example, tab 305 can allow for a user to open closure 302 even when the user is wearing gloves.

FIG. 5A illustrates certain embodiments of an applicator system 50 comprising a storage device 52 configured to receive applicator device 10. Storage device 52 may comprise a wall 500 and a bottom 502 that define a chamber 504. In certain embodiments, wall 500 and/or bottom 502 may be transparent. In certain embodiments, wall 500 and/or bottom 502 may be translucent. In certain embodiments, wall 500 and/or bottom 502 may be opaque. Storage device 52 may comprise various cross-sectional geometries including, but not limited to, circular, oval, rectangular, triangular, polygonal, or complex shapes comprising a combination thereof.

In certain embodiments, applicator device 10 may be inserted into and/or removed from chamber 504 of storage device 52, thereby exposing substantially hydrophilic foam 112 and/or abrasion layer 114 to a fluid 506. In certain embodiments, storage device 52 may comprise a seat 508. Seat 508 may include one or more angled regions 510 that may define a well 512 to at least partially contain fluid 506. As illustrated by FIG. 5B, in certain embodiments, angled regions 510 may generally correspond to certain surfaces of substantially hydrophilic foam 112 and/or abrasion layer 114, so as to facilitate contact between substantially hydrophilic foam 112 and/or abrasion layer 114 and fluid 506. As a result, fluid 506 may be more efficiently transported between substantially hydrophilic foam 112 and/or abrasion layer 114 and well 512 for later dispensing. Although FIGS. 5A-8B illustrate substantially hydrophilic foam 112 and/or abrasion layer 114 mating to the respective angled regions (e.g., 510), one skilled in the art would realize that possible aberrations in mating can occur due to, e.g., various manufacturing tolerances.

Still referring to certain embodiments as illustrated by FIG. 5B, endpiece 108 may attach to storage device 52 to form an interface 514. Endpiece 108 and wall 500 may form a seal 516 generally located at interface 514. Seal 516 may substantially prevent various contaminants from entering chamber 504 and/or fluid 506. As a result, the sterility of certain components within chamber 504 (e.g., handle 104, base 102, substantially hydrophilic foam 112 and/or abrasion layer 114, seat 508 and/or fluid 506) may be ensured. In certain embodiments, seal 516 may be formed by placing a compliant material (e.g., rubber) between endpiece 108 and wall 500. In certain embodiments, seal 516 may be formed by various mechanisms known in the mechanical arts, including, but not limited to, threaded screw-type mechanisms, press-fit and/or slip-fit mechanisms, friction-fit mechanisms, and the like, or combinations thereof.

According to certain embodiments, as illustrated in FIGS. 6A-6C, handle 100 may extend or retract to allow for a larger or smaller applicator system 50. In this manner, in certain embodiments, applicator device 10 and/or applicator system 50 can facilitate certain space-saving design considerations. In certain embodiments, endpiece 108 and wall 500 may form a seal, as described in more detail above. As illustrated in FIG. 6B, handle 100 may be comprised of an upper portion 600 and a lower portion 602. In certain embodiments, lower portion 602 may slide within upper portion 600 in a telescoping manner. In certain embodiments, upper portion 600 may slide within lower portion 602. Other ways exist in which handle 100 may extend and/or retract including, but not limited to, an accordion-style collapsing of either or both upper portion 600 and lower portion 602, a threaded mechanism that allows for extension and/or retraction by twisting upper portion 600 relative to lower portion 602, and/or a folding of upper portion 600 onto lower portion 602 through the use of, e.g., a hinge located between upper portion 600 and lower portion 602. Interconnect 604 may define a transition between upper portion 600 and lower portion 602. In certain embodiments, interconnect 604 may be located at approximately the center of handle 100. In certain embodiments, interconnect 604 may be located away from the center of handle 100. In certain embodiments, interconnect 604 may incorporate a locking mechanism to hold handle 100 in an extended state. Locking mechanisms are well known in the art and include, but are not limited to, spring-loaded mechanical stops.

Figure 7C:
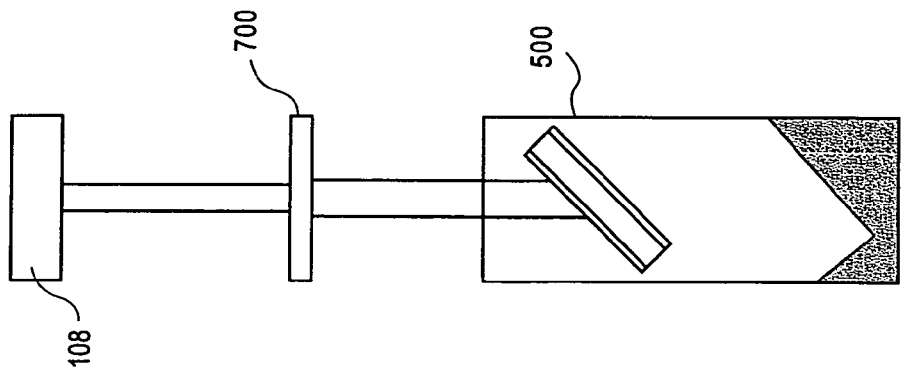
FIG. 7C illustrates a side view of an applicator system with an intermediate endpiece and an extended handle with an applicator device that is partially removed, according to certain embodiments.
Figure 7B:
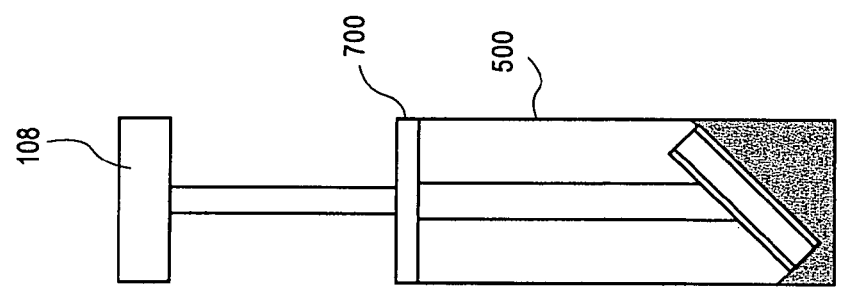
FIG. 7B illustrates a side view of an applicator system with an intermediate endpiece and a retractable handle in an extended position, according to certain embodiments.
Figure 7A:
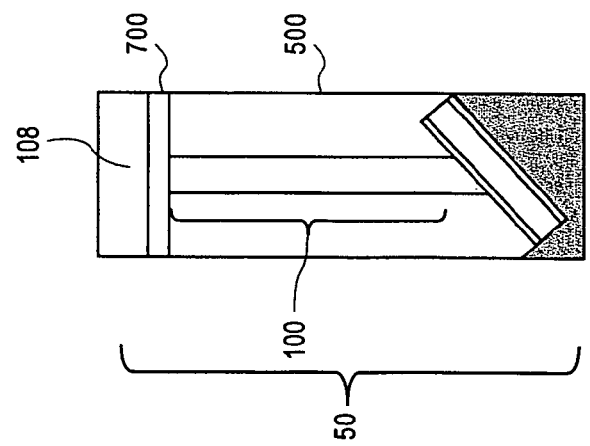
FIG. 7A illustrates a side view of an applicator system with an intermediate endpiece and a retracted handle, according to certain embodiments.

According to certain embodiments, as illustrated in FIGS. 7A-7C, applicator system 50 may comprise an intermediate endpiece 700. Intermediate endpiece 700 may allow handle 100 to extend and/or retract while intermediate endpiece 700 retains contact with wall 500. As a result, any seal formed between intermediate endpiece 700 and wall 500 continues to prevent certain unwanted contaminants from entering chamber 504, even while handle 100 is extended or retracted.

Figure 8A:
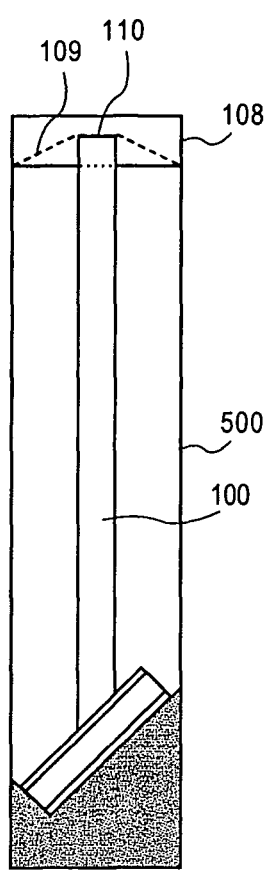
FIG. 8A illustrates a side view of an applicator system with a removable endpiece, according to certain embodiments.
Figure 8B:
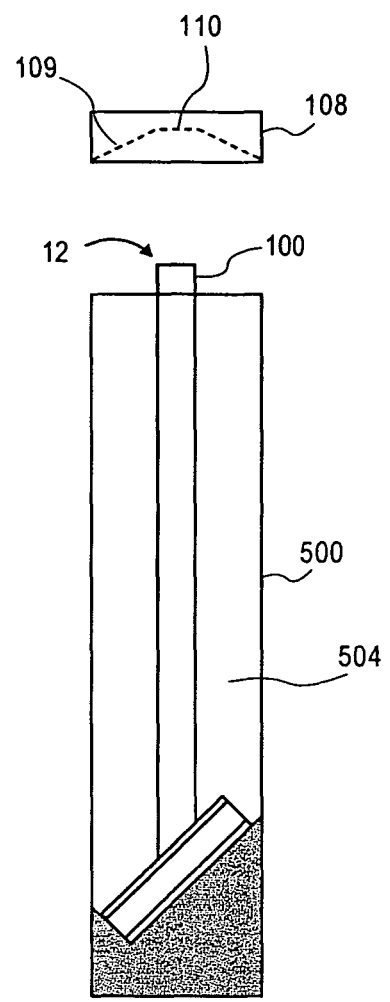
FIG. 8B illustrates a side view of an applicator system with a removable endpiece removed, according to certain embodiments.

According to certain embodiments, as illustrated in FIGS. 8A-8B, endpiece 108 may be removed from handle 100. Endpiece 108 may be attached to handle 100 in a variety of ways known in the art including, but not limited to, press-fits, friction-fits, threaded attachments, screws, adhesives, and the like. In certain embodiments, endpiece 108 can comprise a cavity. In certain embodiments, the cavity can be conical in shape. For example, the cross-section of the cavity can comprise an angled portion 109 and a flat portion 110 wherein angled portion 109 can direct handle 100 toward flat portion 110 as endpiece 108 is attached to storage device 52. That is, in certain embodiments, the cavity can locate handle 100 in the center of storage device 52 as endpiece 108 is connected to storage device 52.

According to certain embodiments, the applicator device and/or the applicator system may be sterilized in various ways known in the art including, but not limited to, exposure to ethylene oxide ("(Et)$_2$O"), gamma radiation, electron beam, and/or steam. According to various embodiments, the fluid may be sterilized in various ways known in the art including, but not limited to, filtration, exposure to gamma radiation, electron beam, and/or steam. For example, U.S. Pat. No. 6,682,695 discloses a method for sterilizing a fluid that can be consistent with certain embodiments of the invention.

According to certain embodiments, as illustrated by FIGS. 5A-5B, applicator device 10 may be inserted into storage device 52 to place substantially hydrophilic foam 112 and/or abrasion layer 114 (see, e.g., FIG. 4A) in contact with fluid 506. After insertion, endpiece 108 may form a seal with wall 500 of storage device 52 through, for example, a screw mechanism. As substantially hydrophilic foam 112 and/or abrasion layer 114 contacts fluid 506, fluid 506 may transfer to substantially hydrophilic foam 112 and/or abrasion layer 114. While applicator system 50 is sealed, applicator system 50 may be sterilized by exposure to, for example, (Et)$_2$O, gamma radiation, electron beam, and/or steam. Once an area for treatment has been targeted, a user may unseal endpiece 108 from wall 500 by, for example, unscrewing endpiece 108. Thereafter, applicator device 10 may be removed from storage device 52, including substantially hydrophilic foam 112 and/or abrasion layer 114, which may contain fluid 506. The user may then abrade the epidermis of the area selected for treatment using abrasion layer 114 (see, e.g., FIG. 4A), in a rubbing or scraping manner. When desired, the user may apply pressure to applicator device 10, thereby compressing substantially hydrophilic foam 112 and/or abrasion layer 114 to release a desired amount of fluid 506 into the targeted area.

Example 1: The effectiveness of the applicators was evaluated using a Pig Skin Model conducted under controlled laboratory conditions. This controlled laboratory model was devised to simulate clinical dermal use of the applicators to deliver and apply antimicrobial solutions to the skin. The use of this controlled laboratory model allowed the determination of the effectiveness of the applicator and an antimicrobial solution in reducing bacterial counts on the skin.

Olanexidine [1-(3,4-dichlorobenzyl)-5-octylbiguanide] was the active ingredient of an antiseptic solution tested with four different embodiments of the applicator invention described herein. The reduction in the colony counts of the bacteria on the surface of the Pig Skin was determined; the $Log_{10}$ units were used for the expression of the counts. This method of expressing the number of colony forming units is recommended in the requirements in the Tentative Final Monograph for Health-Care Antiseptic Drug Products; Proposed Rule, dated Jun. 17, 1994. In the Pig Skin study, the number of colony forming units was determined.

In in vitro studies designed to determine the olanexidine minimum inhibitory concentration ("MIC") of a wide range of bacteria, olanexidine was shown to inhibit >95% of 1050 organisms with ≤32 μg/ml of olanexidine solution. The bacteria included in the MIC testing study included clinical isolates from a number of bacterial and fungal species. The MIC method is a widely accepted methodology that is useful for determining and comparing in vitro antimicrobial activity, while the Pig Skin Model is useful for determining activity under simulated conditions of use. The following chart summarizes the results obtained with the Pig Skin Model:

TABLE 1

EXPERIMENTAL APPLICATOR DESIGN EVALUATIONS
PIG SKIN MODEL EVALUATION
Using 0.91% Olanexidine Aqueous Solution
2 Minute Application Time

| Sponge/Gauze Laminate Description | Actual $Log_{10}$ Reduction |
|---|---|
| Hydrophilic Foam, laminated with 1 ply Abrasion Layer | 1.32 |
| Hydrophilic Foam, laminated with 2 ply Abrasion Layer | 1.73 |
| Hydrophilic Foam, laminated with 3 ply Abrasion Layer | 2.02 |
| Hydrophilic Foam, laminated with 4 ply Abrasion Layer | 1.55 |

Other various embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An applicator system, comprising:
   (a) an applicator device for applying a topical antiseptic to a subject's skin, said device comprising:
      a handle comprising a proximate end and a distal end;
      a base coupled to the proximate end of the handle;
      a substantially hydrophilic foam coupled to the base;
      an endpiece coupled to the distal end of the handle;
      the topical antiseptic; and
      at least one abrasion layer coupled to the substantially hydrophilic foam, wherein the at least one abrasion layer is configured to abrade the subject's skin; and
   (b) a storage device comprising a wall and a bottom surface that defines a chamber therebetween, wherein the endpiece of the applicator device is configured to engage with the wall of the storage device to form a seal that substantially prevents contaminants from entering the chamber when the applicator device is inserted into the chamber.

2. The applicator system of claim 1, wherein the topical antiseptic is retained in the substantially hydrophilic foam.

3. The applicator system of claim 1, wherein the applicator device and the storage device are sterilized.

4. The applicator system of claim 3, wherein the topical antiseptic is sterile.

5. The applicator system of claim 1, wherein the topical antiseptic includes at least one active ingredient chosen from ethanol, isopropyl alcohol, other alcohols, and combinations thereof; benzalkonium chloride; benzethonium chloride; chlorhexidine gluconate; chloroxylenol; coflucarban; flourosalan; hexachlorophene; hexylresorcinols; iodine containing compounds; biguanide derivatives (or a salt thereof); povidone iodine; povidone iodine with ethanol, isopropyl alcohol, other alcohols, and combinations thereof.

6. The applicator system of claim 5, wherein the at least one active ingredient is a biguanide derivative or a salt thereof.

7. The applicator system of claim 6 wherein the biguanide derivative or salt thereof is olanexidine [1-(3,4-dichlorobenzyl)-5-octylbiguanide] or a salt thereof.

8. The applicator system of claim 6, further comprising a polyoxyethylene-based nonionic surfactant.

9. The applicator system of claim 8, wherein the nonionic surfactant is at least one surfactant selected from Poloxamer 124, POE (9) lauryl ether, and POE (10) lauryl ether.

10. The applicator system of claim 8, wherein the biguanide derivative or a salt thereof is present at a concentration of about 0.05 to about 5.0% (w/v of biguanide base) and the polyoxyethyltene-based nonionic surfactant is present at a concentration of about 0.05 to about 16% (w/v).

11. The applicator system of claim 1, wherein the at least one abrasion layer comprises a textured and/or woven material.

12. The applicator system of claim 11, wherein the at least one abrasion layer includes a gauze material, which comprises cotton, rayon, nylon, or combinations thereof.

13. The applicator system of claim 1, wherein the at least one abrasion layer includes a plurality of abrasion layers in which at least one of the plurality of abrasion layers is coupled to the substantially hydrophilic foam.

14. The applicator system of claim 1, wherein the base of the applicator device is removable.

15. The applicator system of claim 1, wherein the handle of the applicator device is extendable.

16. The applicator system of claim 1, wherein the handle is configured to extend in a telescopic manner.

17. The applicator system of claim 1, wherein the handle of the applicator device is configured to extend and retract in a telescopic manner.

18. The applicator system of claim 1, wherein at least a portion of the handle of the applicator device includes a surface coating.

19. The applicator system of claim 1, wherein at least a portion of a surface of the handle of the applicator device includes a texture.

20. The applicator system of claim 1, wherein the handle of the applicator device comprises at least one indentation.

21. The applicator system of claim 1, wherein the handle of the applicator device comprises at least one protrusion.

22. The applicator system of claim 1, wherein the handle of the applicator device comprises at least one hollow region.

23. The applicator system of claim 22, wherein the handle of the applicator device comprises at least one substantially sealable membrane configured to provide access to the hollow region of the handle and through which topical antiseptic may be introduced or withdrawn.

24. The applicator system of claim 22, wherein the hollow region is configured to receive the topical antiseptic by at least one of the following: directly and indirectly.

25. The applicator system of claim 1, wherein the handle and the base of the applicator device define an angle.

26. The applicator system of claim 25, wherein the angle is about 45 degrees.

27. The applicator system of claim 25, wherein the angle is adjustable.

28. The applicator system of claim 1, wherein the storage device comprises a seat that forms a well for holding the topical antiseptic.

29. The applicator system of claim 1, wherein the applicator system is provided in ready to use form.

30. The applicator system of claim 1, wherein the handle is solid.

31. The applicator system of claim 1, wherein at least a portion of the wall of the storage device is transparent or translucent.

32. The applicator system of claim 1, wherein at least a portion of the wall of the storage device is opaque.

33. The applicator system of claim 1, wherein a cross-sectional shape of the storage device is one of circular, oval, rectangular, triangular, or polygonal.

34. An applicator system for a topical antiseptic, comprising:
   (a) an applicator device for applying the topical antiseptic to skin, the device including:
      a handle;
      a base coupled to one end of the handle;
      a substantially hydrophilic foam coupled to the base;
      an endpiece coupled to the handle; and
   (b) a storage device including: a wall and a bottom surface that defines a chamber therebetween, wherein the endpiece of the applicator device is configured to engage with the wall of the storage device to form a seal that substantially prevents contaminants from entering the chamber when the applicator device is inserted into the chamber.

35. The applicator system of claim 34, further including the topical antiseptic retained in the substantially hydrophilic foam.

\* \* \* \* \*